(12) United States Patent
Coleman

(10) Patent No.: US 11,589,799 B1
(45) Date of Patent: Feb. 28, 2023

(54) METHOD AND SYSTEM FOR MONITORING AND PROVIDING BENEFICIAL VISUAL AND AUDITORY STIMULATION FOR DEMENTIA PATIENTS

(71) Applicant: James A. Coleman, Memphis, TN (US)

(72) Inventor: James A. Coleman, Memphis, TN (US)

( * ) Notice: Subject to any disclaimer, the term of this patent is extended or adjusted under 35 U.S.C. 154(b) by 339 days.

(21) Appl. No.: 16/848,815

(22) Filed: Apr. 14, 2020

(51) Int. Cl.
| | |
|---|---|
| *G16H 40/67* | (2018.01) |
| *G16H 80/00* | (2018.01) |
| *A61B 5/00* | (2006.01) |
| *A61B 5/1171* | (2016.01) |
| *A61B 5/11* | (2006.01) |
| *G06F 3/16* | (2006.01) |
| *G06F 21/31* | (2013.01) |
| *G06F 21/32* | (2013.01) |
| *G06V 40/16* | (2022.01) |
| *A61M 21/00* | (2006.01) |

(52) U.S. Cl.
CPC .......... *A61B 5/4088* (2013.01); *A61B 5/0004* (2013.01); *A61B 5/0015* (2013.01); *A61B 5/1112* (2013.01); *A61B 5/1176* (2013.01); *A61B 5/6803* (2013.01); *A61B 5/6898* (2013.01); *A61B 5/742* (2013.01); *A61B 5/7405* (2013.01); *G06F 3/167* (2013.01); *G06F 21/31* (2013.01); *G06F 21/32* (2013.01); *G06V 40/16* (2022.01); *G06V 40/172* (2022.01); *G16H 40/67* (2018.01); *G16H 80/00* (2018.01); *A61M 2021/005* (2013.01)

(58) Field of Classification Search
CPC combination set(s) only.
See application file for complete search history.

(56) References Cited

U.S. PATENT DOCUMENTS

| | | | |
|---|---|---|---|
| 2018/0336962 A1* | 11/2018 | Cronin | A61B 5/14552 |
| 2021/0209362 A1* | 7/2021 | Wexler | G06V 40/20 |
| 2021/0225391 A1* | 7/2021 | Wexler | H04R 1/326 |
| 2021/0320801 A1* | 10/2021 | Wyss | G06V 40/171 |
| 2021/0374468 A1* | 12/2021 | Chandraker | G06T 3/0006 |
| 2022/0027629 A1* | 1/2022 | Case | A61B 1/0004 |
| 2022/0148697 A1* | 5/2022 | Woodyear | A61J 1/065 |
| 2022/0150592 A1* | 5/2022 | Nishimura | H04N 21/4668 |
| 2022/0180342 A1* | 6/2022 | Eaton | G06Q 10/30 |
| 2022/0181020 A1* | 6/2022 | Keshavjee | G06F 3/013 |

* cited by examiner

*Primary Examiner* — Helen Zong
(74) *Attorney, Agent, or Firm* — William S. Parks

(57) ABSTRACT

An on-person portable device and/or app that allows for constant location monitoring of dementia patients is disclosed. Such a device and/or app also includes automated communication of facial recognition of persons proximally near such a patient as well as possible generation of certain music in response to patient status and/or location. The patient is provided the device and/or app for handling or wearing, such as a phone or pair of glasses, in order to follow location through GPS monitoring, and a reactive program therein that automatically views another person and provides an identification thereof coupled with a voice modulator within an earpiece or like device for memory stimulation pertaining to loved ones or friends, and the like. The same program may also provide the music response to comments, movement, or any other external stimuli to the subject patient, again, to evoke a memory stimulus, as well.

4 Claims, 3 Drawing Sheets

FIG. A

METHOD AND SYSTEM FOR MONITORING AND PROVIDING BENEFICIAL VISUAL AND AUDITORY STIMULATION FOR DEMENTIA PATIENTS

FIELD OF THE DISCLOSURE

The present disclosure relates to an on-person portable device and/or app that allows for constant location monitoring of dementia (and like) patients. Such a device and/or app also includes automated communication of facial recognition of persons proximally near such a patient (for instant memory stimulation) as well as possible generation of certain music in response to patient status and/or location. In such a system and method, the patient is provided the device and/or app for handling or wearing, such as a phone or pair of glasses, in order to follow location through GPS monitoring, and a reactive program therein that automatically views another person and provides an identification thereof coupled with a voice modulator within an earpiece or like device for memory stimulation pertaining to loved ones or friends, and the like. The same program may also provide the music response to comments, movement, or any other external stimuli to the subject patient, again, to evoke a memory stimulus for improved functionality. The method of utilizing such a device for such various end-uses is also encompassed within this invention.

BACKGROUND OF THE INVENTION

Difficulties arise as the population ages around the world. With improvements in medical technology, life spans increase leaving a greater number of elderly persons that require a certain degree of attention to assure that everyday activities and general health issues are acceptable for such a population segment. Additionally, such aging members of society do not commonly seek living arrangements in a nursing home facility or communal location. Although some elderly persons are placed in such around-the-clock and/or close-quarter situations, many others desire to live in their own homes or apartments, whether it be for financial, logistical, or other reasons. It has further been well-documented that short-term memory loss may be reduced for patients that remain in familiar surroundings and, even with removal from such an environment for as short as a few days, such a patient may suffer unfortunate consequences in this manner. Thus, the benefits of having elderly or other patients susceptible to short-term memory loss issues staying in their own homes are quite substantial. As such, family and friends generally seek suitable methods of monitoring such self-sustaining elderly, etc., persons to ensure safety and health concerns are properly met.

Furthermore, there are people within a narrower segment of society that face the unfortunate issues of early onset dementia while also desirous of sustaining his or her own household. Such a situation may not automatically cause a caregiver or family member to seek professional help, such as a nursing home or like facility, for constant monitoring and safety issues; actually, with early onset of such a disease or condition (such as, for example, Alzheimer's) a patient may exhibit short-term memory loss or other reduction in mental capacity at that point and certain activities or therapeutic methods utilizing the patient's mental faculties may help to prevent further deterioration. Constant presence of a caregiver for such a purpose may prove too expensive for such an endeavor. As well, the lack of a familial subject to aid in such a mental exercise through voice and visual commands and/or stimulations militates against the utilization of an outside subject for such a purpose in many situations. However, the constant presence of a family member (or like close friend, as one example) may not prove feasible, either, as such a person may not have the time, resources, and wherewithal to provide such around-the-clock attention. Memory stimulation from a suitable source may thus provide the desired therapeutic effect while allowing the patient to remain in their own familiar surroundings.

As such, there exists a definite need to provide a beneficial system, method, and/or device that allows for constant monitoring as well as providing potential therapeutic mental exercises for a patient. Such a device should not rely solely on the patient's input or activity in order to enable a monitoring system to operate. Likewise, such a system should not prove appreciably invasive into the patient's life (through, for example, constant video monitoring). Additionally, any constant video monitoring would prove extremely difficult for a monitor to undertake throughout an entire day, not to mention the privacy issues the patient would not want to lose. As a result, any such system would necessarily allow for an interested and authorized party to elicit a proper response from the patient directly through the system, as well as the capability to either generate on demand a mental exercise program or the ability of such an interested and authorized party to set up a pre-scheduled session (or multiple daily sessions) of such a mental exercise program for the patient's benefit.

In the past, and up to today, the industry that pertains to helping monitor family members has centered on broad tracking, video viewing, and/or self-reporting devices. For instance, personal tracking devices have been found to be useful in locating missing persons. Such tracking devices typically use a network of Global Positioning Satellites (GPS) in low earth orbit that broadcast precise timing signals from on-board atomic clocks. Using triangulation formulas, a device that picks up signals from several satellites simultaneously can determine its position in global coordinates, namely latitude and longitude. Thus, an object and/or person carrying the GPS device may be located provided the appropriate equipment and trained personnel are available for determining the location of the GPS device. Such devices are clearly limited to situations that concern placement of proper reporting/monitoring phones, computer chips, and the like, and offer after-the-fact help once a person has gone missing. Such devices also provide nothing beyond a tracking benefit; therapeutic and/or responsive reporting is unavailable.

There are standard systems in place today that include audio as well as, in some circumstances, audiovisual communications, in nursing homes and like facilities. Such devices are used primarily as communication devices as well as for emergency notification purposes. Beyond that, however, such systems are rather limited in that communications are reliant upon the activity of a patient/tenant and are generally located in specific facilities. Otherwise, the utilization of cell phones and/or computers serve much the same purpose. In terms of providing overall services for patients suffering from dementia, memory loss, or other like symptoms, there is no component within such systems and processes that takes into account such a specialized type of situation. With the potential for decreased mental capacity, a patient's ability to properly operate and/or activate such a device is highly suspect. Such a lack of direction in that respect thus limits the usefulness of such a typical communication system and leaves a rather significant portion of society without suitable offerings to not only help such patients in terms of therapeutic benefits, but do not allow for automatic notifications if lack of communication from a patient occurs.

Likewise, there are devices that patients may keep with them constantly to permit instant notification of health problems. Such devices that are worn by a user for the purpose of instantaneous notification of health or status difficulties have been utilized for many years. Although such devices may provide a certain degree of comfort to both user and family members (or friends) that reports of such problems may be handled quickly and reliably, such may not be the case with patients suffering from certain degrees of memory loss and other dementia maladies. In actuality, the requisite active nature of such self-reporting devices forces the user to remain vigilant, both in terms of remembering the availability, if not presence, of such a signal device on their person, but the failure of activation likewise prevents proper communication with the necessary authorities and/or family members that any problem is at hand. These devices thus fail to permit an outside party from communicating with the user and thus relies solely upon the user's capacity to understand and activate the device itself. Again, in situations with dementia patients, at least, such a requirement is deficient as to the reliability such a system actually provides all parties involved.

As it stands, although certain systems do exist to allow for both communication with patients in homes, rooms, and other like locations, these are limited to communication alone. There is no consideration with the importance that memory stimulating programs, particularly in terms of immediate facial recognition coupled with identification and auditory statement thereof to such a patient, let alone the generation of a musical piece such a patient may associate with certain conditions and/or places, can provide (particularly in a potentially therapeutic environment for early onset dementia patients). Likewise, mere distress reporting devices do not allow early onset dementia patients full potential in terms of reliability that status reports will be made timely and properly. The ability to compensate for such reliability deficiencies, as well as the capability of providing at least a combination of therapeutic memory stimulation programs and status reports from such patients to any number of authorized interested outside parties would be highly beneficial to this growing segment of society. As of today, however, such a system and/or device is unavailable within the remote report/dementia patient treatment industry.

ADVANTAGES AND DESCRIPTION OF THE DISCLOSURE

The present disclosure thus provides the advantage of simultaneously offering a hand-held or person-mounted monitoring device and system and an auditory presentation (or presentations) in order for a person located at the same location as the device and system to experience the benefit of facial recognition and/or programmed musical recordings in response to certain situations. Another advantage is that a remote party may also monitor the subject patient through a linked app or program and provide his or her own stimulus to such a patient on demand through the system. Additionally, the system and device offer the advantage that any lack of timely communication of status in response to such a message will generate an monitoring alarm for others and a musical recording for the subject patient for calming purposes.

Accordingly, the disclosure encompasses a combination monitoring and communication system for utilization with a remote patient/user, wherein said system comprises: i) a first device residing with said remote patient that includes a base monitoring capability including a speaker function that allows an outside party to listen to the immediate environment of said remote patient/user, as well as to receive and send auditory signals thereto such an outside party, said first device further including a signal component for GPS tracking of said remote patient/user, and ii) at least one monitoring/communication device residing with at least one outside party, said at least one monitoring/communication device comprising a direct line auditory portal for listening to said remote patient/user environment and communicating with said remote patient/user on demand, a GPS tracking module associated with said GPS signal of said first device, and an auditory and/or video communication module for supplying music, sounds, and/or videos to said remote patient/user on demand. The system may further comprise a database of photographs of selected individuals' faces for facial recognition and identification thereof within at least the first device, wherein the database is associated with said speaker function to provide auditory identification of a recognized individual to said remote patient/user. The first device database may further include auditory recordings of individual voices for identification thereof for the remote patient/user, as well. A method of utilizing such a combination device system is also encompassed herein, with the first device provided to the remote patient/user and being initialized to provide monitoring thereof such a remote patient/user through association with at least one monitoring/communication device to at least one outside party that itself becomes initialized and thus associated with the first device, thereby allowing the at least one outside party the ability to monitor, communicate, track, and transfer auditory/visual presentations to the remote patient/user. The devices may then be activated allowing the at least one monitoring/communication device to monitor through audio capability the remote patient/user, thus allowing the at least one outside party to select any or all combinations of the monitor, communicate, tracking, and auditory/visual transfer abilities in association with the remote patient/user. The method may also include the facial and auditory recognition capabilities noted above for the remote patient/user. The devices noted above, whether of the remote patient/user or the at least one outside party, may be portable and/or worn or hand-held in nature, or may also be, if desired, placed on surfaces (such as desk top computers, for example).

Said disclosure thus also encompasses the overall method of providing a memory stimulation presentation to said remote patient through the utilization of said video screen through the activation of a program including at least one visual picture or film, wherein said memory stimulation presentation is coupled to a stop or reset activation switch to be operated by said remote patient upon receipt of said memory stimulation presentation; said method further comprising the step of notifying at least one authorized outside party of the failure of said remote patient to activate said stop or reset activation switch within a suitable amount of time subsequent to initiation of said memory stimulation presentation, wherein said at least one authorized outside party may then discontinue said notification step upon receipt of a proper communication with said remote patient.

As noted above, such an inventive system/device/method allows for any number of people to remain in their own homes with a reliable method of communication and notification if any problems ensue in such a situation. Early onset dementia, in particular, has proven rather troublesome to handle for many people. Such patients do not exhibit long-term problems with memory loss or other typical dementia issues, and thus would like to enjoy the independence of their own surroundings while also having security that should any health or safety issues arise then such people (patients) can rely upon the inventive system to notify loved ones or other authorized persons to help. Additionally, though, the issues involved with early onset dementia (or early onset Alzheimer's, or other like conditions) leave such persons prone to memory loss that may actually be treated through certain therapeutic activities, such as, for instance, repetitive or long-term presentations of pictures of family members or other close acquaintances, as well as films or other video presentations of certain settings, activities, remembrances, and the like. In such a manner, it has been found that such patients may, through such presentations, exhibit proper stimulation of motor neurons and other brain activity that enhances and, at least, curtails memory loss in many such patients. With early onset cases, then, the ability to provide such an effect, particularly through a remote control system, or, otherwise through a pre-programmed device, accords such a patient with an effective manner of memory stimulation in a regimented fashion, such as daily, every few hours, even hourly (the regimen may be programmed in any manner to effectuate any time interval for such a memory stimulation presentation).

Although there are other devices that accord memory stimulation activities, there are none that combine such an action with a status notification method as well. As such, the utilization of the inventive device/system may be undertaken at any location that allows for a remote patient (i.e., an early onset dementia patient, or one exhibiting a similar condition, as described above) to enjoy a certain degree of independence, such as his or her own home or apartment. As such, although community living centers and nursing home facilities may be equipped with such a device, the versatility of such a system/device allows greater freedom and reliability when put into practice. The potential for a remote patient then to have such a memory stimulation event initiated in a regimental fashion provides only one portion of the overall system/device benefit and effect.

Additionally, then, and importantly, the system/device accords the remote patient/user and an authorized outside party (such as, for instance, a family member or a friend that has been added as a person to be contacted in association with the overall system/method herein described) the security that not only is the remote patient being presented memory stimulation activities, but also a notification step to the outside party if warning signs and/or signals are generated in relation to the patient status. Such a status assessment of the remote patient may thus be monitored by the system itself and provides indications of any non-standard or -expected activities, comments, or other difficulties (awkward/haphazard movements and/or sounds, for instance) exhibited by the monitored patient.

Additionally, the overall system/method includes the capability for an authorized outside party to discontinue the monitoring process for a period of time, if desired, and transfer the same capability to another outside party. Of course, multiple parties may monitor simultaneously, if desired, as well.

The system thus includes the device and/or app providing the needed video representation, preferably through a video screen, preferably of an Liquid Crystal Display (LCD) type (although any type of such visual display may be utilized, including plasma, transistor, vacuum tube, etc., technologies), and preferably conveying color to the remote patient (at least in association with the facial recognition component). Such a screen would have the capability of recognizing a person's face and accessing, through the device, a database for identification thereof. Such may then, upon recognition and identification, be provided as a color (or other type) photograph within the screen for the patient to review and couple such a visual stimulus to an auditory presentation of the name (if linked with a face on the database) thereof for the patient to receive and hopefully process for such a stimulus purpose. In essence, the system/device includes a proper audiovisual component for video presentations of such recognized faces and generation of the associated name thereof for announcement to the patient.

Additionally, the device/system may further include a component that allows for notification to an outside party if a person comes within the vicinity of the user and is not recognizable within the identification database, particularly if such a person is present proximal to the user for a certain amount of time. In other words, beyond the ability to have the user utilize the device/system to direct the app/phone/device towards a person (or the device may pick up auditory sounds such as the person's voice that may within the database as well) to aid in identifying such a person (particularly if the user suffers from memory loss, of course), if such a person is not identifiable through the database, the system/device may provide the ability to warn an outside party (or parties) if such a person is more than just a passing individual and thus may potentially harm the user. Furthermore, the app/device may also include the capability of snapping a picture of the person (if aimed in the direction, of course) for recordation and/or sharing with an outside party to help with any such identification if the person does not exist in the pictorial and/or auditory database. Such an option thus allows the user and outside party further aid in protecting the user if he or she remains on their own.

The basic device/system then will include a computer component that properly stores and, upon activation through any number of stimuli, initiates the audiovisual presentation as needed to accord with the remote patient's memory of recognized faces within the system itself. The computer is programmed with such a facial recognition database with the coupled audio track of such a name, for such a purpose, as well as, as alluded to above, the possible auditory records of a person speaking with identifications related thereto for such a purpose.

Thus, the computer will initiate such a memory stimulation activity, including the audiovisual clip (picture, film, or both, for instance) until the remote patient possibly reacts through agreement with the system's identification of such a person. Additionally, as alluded to above, the remote patient may be monitored in relation to outward stated (commentary) status or movements through GPS tracking. In any event, if needed, such a system may be programmed to respond to certain feelings, movements, even geographical placement of the remote patient with the generation of a specialized musical recording, again, associated with certain situations/feelings, locations, as a musical stimulus for the subject remote patient, too. Such a musical recording may include a calm, reassuring, and soothing piece, or may be one that the remote patient has already been accustomed to, particularly in relation to similar situations and locations.

Such communications may be undertaken by any number of a variety of instruments and devices. Telephonic means (through the device and/or app. for example) are possible, as described above. Additionally, though, wireless means may be implemented and utilized for such purposes. For instance, the remote patient may have a portable device or, preferably, at least in one non-limiting embodiment described herein, a wall- or furniture-mounted device that includes a single or bi-directional wireless communication link for transmitting information therefrom to any number of outside parties (through their cellular phones, computers, and the like) via a local hub or receiving station or base station server by way of a wireless radio frequency (RF) link using a proprietary or non-proprietary protocol. For example, within the remote patient's dwelling, a mesh network signal transferring device may be present to send and receive wireless signals Systems having any of the above-described apparatuses in combination with other computer devices, for example, to form a local area network (LAN), a wide area network (WAN), an Ethernet within a building, or an intranet among several geographic locations of a corporation, for example, are contemplated. Also, such signals may be routed wirelessly through WiFi or Bluetooth adapters.

The system/device may also include a calendar and scheduling component in order to alert the remote patient of various events. For instance, if a caregiver is scheduled to visit on specific days and/or at specific daily times, then the computer may be programmed with such reminders that can be easily conveyed to the remote patient, either through a video or audio reminder (with a repeated display of either or both types until the remote patient acknowledges receipt of such a reminder) until the actual event occurs (with intervals of reminders set as desired for such a purpose). Reminders ahead of time may be provided as well of such visits/events and such a reminder activity may also act as a suitable well-being acknowledgement for the remote patient in certain circumstances, if desired. Likewise, such a scheduling component may be utilized for authorized outside parties to remotely add their own scheduled visits on demand, thereby taking advantage of such a reminder system to allow for proper notification of such an upcoming event for the remote patient, too. In essence, such an added system benefit may be utilized for any purpose, including scheduled doctor appointments (and the like), times to prepare for shopping trips (and the like), and any other event that would allow for reminders in such a manner (and thereby allowing for memory stimulation through such a system, as well).

A camera may also be mounted on the device (for any number of reasons, including the communication capability alluded to above) in order to allow for an outside party to view the surroundings of the remote patient if needed. Although a minimal level of invasiveness in envisioned with this overall system/device, if the remote patient is in need of an extra level of security to such an extent, such a camera (like a web cam, for instance) may be utilized as an extra means of monitoring in addition to its utilization as a communication device (as well as possibly film or photograph a person within the vicinity of the user in case such identification is needed).

Thus, in total, the overall device/system/method allows for a combination of memory stimulation and notification to outside parties of the condition of a remote patient without any need for such a patient to hit any type of panic button. Such a passive system/method thus provides both a therapeutic benefit and a reliable safety notification procedure without treading on the independence of an otherwise healthy and self-sustaining patient.

Although such a device/system is envisioned primarily for the benefit of persons with early onset dementia and other like conditions, in actuality it may be utilized in any number of situations, both in terms of types of patients and in locations wherein such a system may be useful. Certain elderly patients may not exhibit dementia symptoms but may need monitoring to ensure their health and safety are not compromised. Utilizing a proper memory stimulus program as noted above, such a system allows for monitoring and potential therapeutic benefits for such patients (even elderly persons without dementia, possibly early onset, or other concerns) as well as the peace of mind for outside monitoring parties that such a patient is taken care of while on their own.

DETAILED DESCRIPTION OF THE DRAWINGS AND EMBODIMENTS

Without any intention of limiting the scope of the disclosed system/device/method, the drawings described herein provide but one embodiment herein. Various modifications and different configurations of such a system/device/method may be employed without deviating from the scope and basis of the present disclosure.

Figure 1:
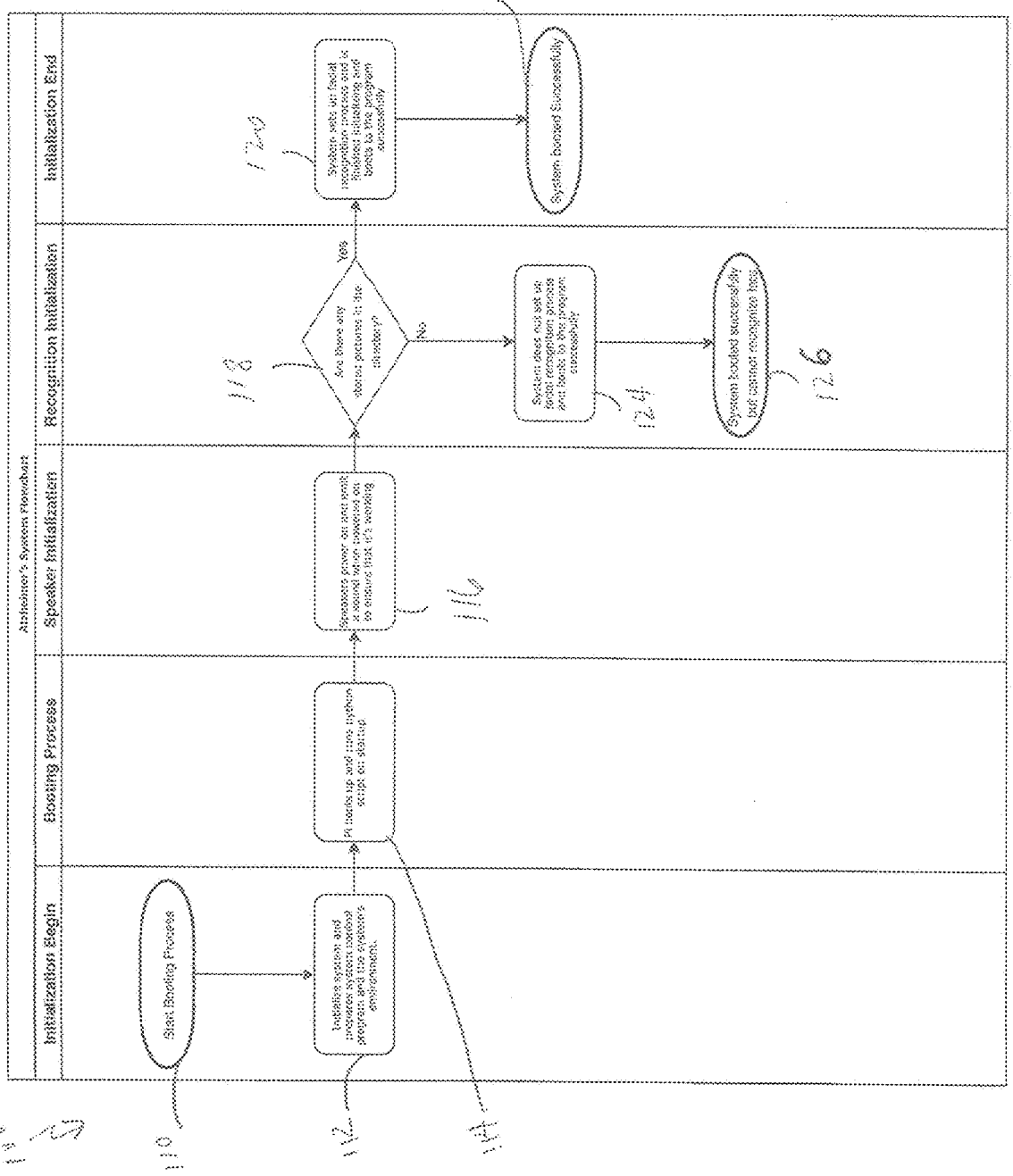
FIG. 1 depicts a flow chart showing one possible embodiment of an overall monitoring device system/method of the disclosure.
Figure 2:
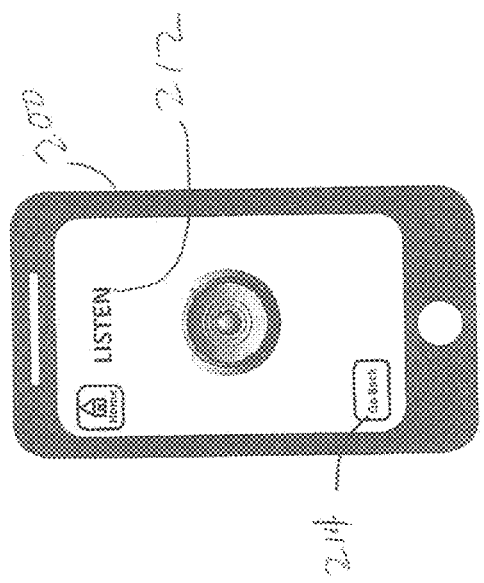
FIG. 2A depicts a possible embodiment of a device/phone screen showing an initial program name for an app associated therewith with which an outside party (or parties) may follow the monitoring system and provide certain operations to the patient/user in response thereto.
FIG. 2B depicts a further device/phone screen of the possible embodiment of FIG. 2A showing a response to clicking or accessing a listen button thereon.
FIG. 2C depicts a further device/phone screen of the possible embodiment of FIG. 2A showing a response to clicking or accessing a GPS button thereon.
FIG. 2D depicts a further device/phone screen of the possible embodiment of FIG. 2A showing a response to clicking or accessing a Music button thereon.

FIG. 1 shows a possible embodiment of a standard flow chart of an overall Alzheimer/early onset dementia patient monitoring and communication system 100 with an initialization step including a booting process 110 to activate the program/app involved which then leads to the initialization of the system 112 in order to prepare the overall control program within the proper environment for the patient/user. Such steps are undertaken in the same manner whether on a phone device or a movable or static computer. The booting process continues with the operation of the program, such as a Pi type, as one non-limiting example, that leads to generation of the needed script (Python, as one non-limiting example) to allow the patient/user to understand and read the instructions and links present within the program at the monitor/phone screen. Subsequent to booting up of the initial system and scripting protocols, the communication/listening speaker system can then initialize for corresponding activities associated with the recognition and/or music components thereof 116. In order to ensure such a speaker component functions properly, the system may be outfitted with a proper notifier therein to provide a sound to alert the patient/user when such a system is up and running and thus ready for any needed operations on demand or in relation to system requirements (facial recognition, for instance, may be implemented automatically for the patient/user with auditory identifications presented in such a manner). After such a speaker set-up, the computer therein may then access any recognition database present for the patient/user's benefit 118 and thus initialize such a component database program within the system for such a purpose. If no such database is present or set-up at that time 124, it may still operate with the other capabilities (music, GPS, etc.) 126. If the database is present 120, the program then merges within the overall system 100 and allows for such facial (auditory, as well, if desired) recognition capability 120 and the system is thus successfully booted up in its entirety 122. In this manner, this embodiment thus FIG. 2A thus provides a possible embodiment of a functions screen program (which may also be considered a Landing page) for a monitoring/communication app associated with this disclosed system. The device 200 (such as, in non-limiting fashion, a smart phone) includes particular identification for the patient/user 202 for easy association thereof by the outside party. The functions available on the device 200 thus include a Listen mode (for direct communication and audio monitoring of the patient/user through the monitoring system) 204, a GPS tracking module 206, a music portal 208 (for supplying therapeutic sounds, music, even possible video presentations to the patient/user through the monitoring system device), as well as a settings button 210 to allow for modifications of certain parts of the app, if needed (volume, shading on the screen, and the like). FIG. 2B shows one possible embodiment of a selected Listen screen (204 of FIG. 2A) with the indicator and speaker link 212 for such possible communication with the patient/user. A return button 214 ("Go Back") is present to allow for the outside party to access the Landing page of FIG. 2A for a different selection. Thus, if the GPS tracking module is selected (206 of FIG. 2A), the possible embodiment of FIG. 2C shows a screen associated therewith with the indicator 216, and a map 218 that associates with the patient/user monitoring device/system and provides a signal thereon the map 218 to show the location of such a person on demand. A return 220 allows, as above, the system to go back to the Landing page (functions screen) of FIG. 2A. A further selection thus may be the possible embodiment of a music portal (210 of FIG. 2A) as shown in FIG. 2D. Upon selection thereof, the outside party accesses such a screen with the indicator 222 that includes the ability to play music through the monitoring system 224, as well as download audio 226 or record audio 228 for such a a purpose. Additionally, as noted herein, such a system may allow for video presentations to be undertaken in like fashion if so desired. In any event, this music portal allows for therapeutic music, sounds, video, and the like, to be provided the target patient/user through the monitoring device/system if needed. The return 230 allows, again, for the outside party to access the Landing page (functions page) of FIG. 2A as well to select a different or, if desired, the same prior module/portal, program on demand.

Figure 3:
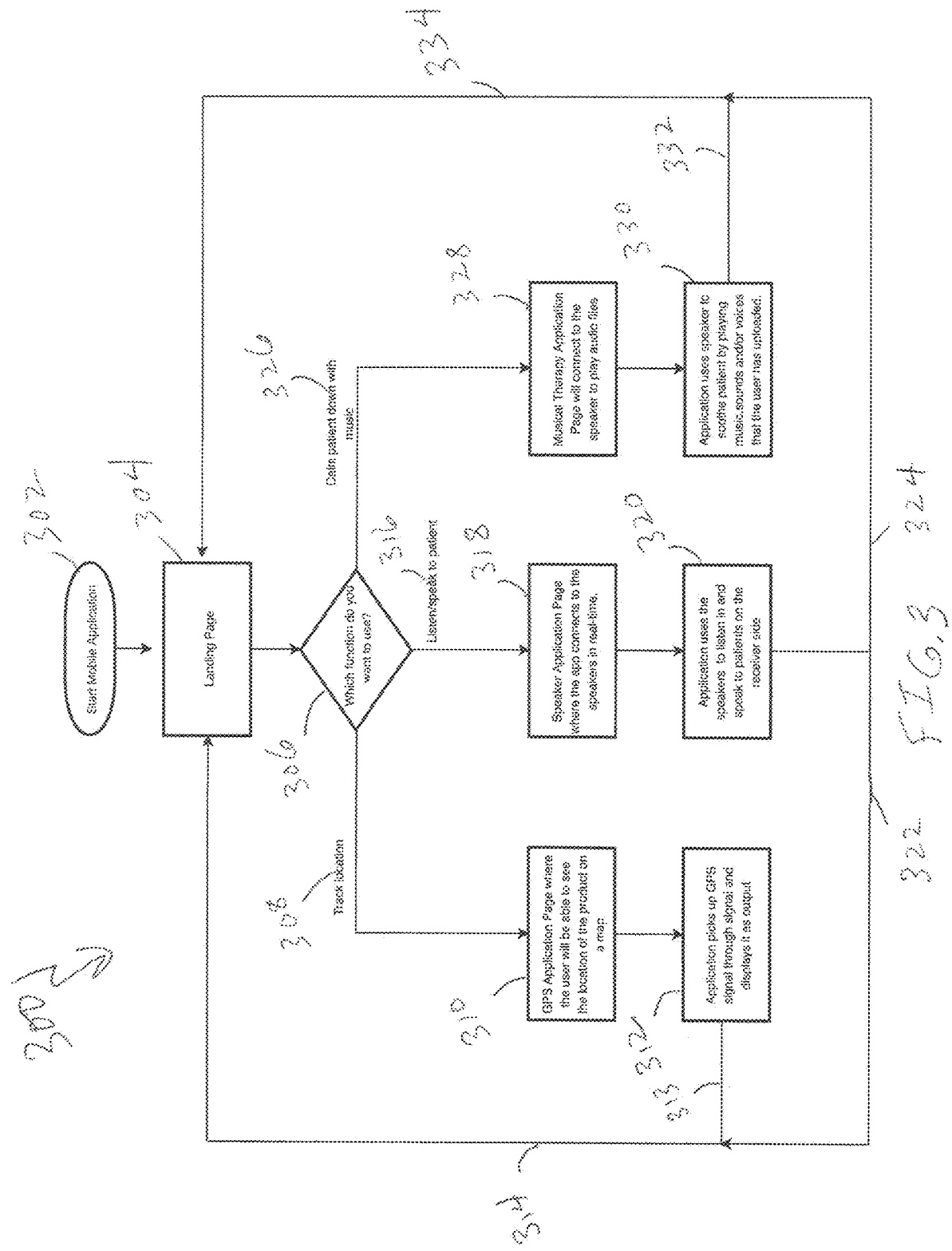
FIG. 3 depicts a possible embodiment of the disclosed communication system for an outside party (or parties) to impart certain actions for the benefit of the monitored patient/user associated with the possible system embodiment of FIG. 1 and utilizing the possible embodiments of FIGS. 2A-2D, through a schematic with the various components therein.

FIG. 3 depicts a schematic 300 of a possible embodiment of the disclosure pertaining to an overall system as booted up with full capacity of facial recognition, music, GPS, and communications between the patient/user and an outside party in relation, for example, to the possible embodiment of the monitoring and communication system shown in FIG. 1. Utilizing, as one non-limiting example, the phone device of FIGS. 2A-2D, the outside party may start a mobile app 302 through selection thereof on the subject device that, again, associates with the patient/user monitoring system described herein. Such a procedure then leads to the initial landing page 304 of the program on the device (again, whether a phone, computer, etc.) to allow the outside party (or parties) the ability to select a function of the system program 306 (as shown, again, as non-limiting examples, within FIGS. 2A-2D, above) in relation to monitoring of the target patient/user. Thus, if the outside party (or parties, as should be well understood is an possibility) determines the there is a need to follow the movement and understand the location of the patient/user, such a tracking option may be selected 308 that accesses the GPS page 310 of the program. This allows the outside party to see the location of the patient/user (or more succinctly perhaps, the patient/user's device if carried) on a map that may be detailed as desired to within feet as a legend. This thus allows the system to find the patient/user's device signal and display such on a map output 312. As this is undertaken, the outside party may then move away from the GPS page 313 and return 314 to the Landing page 304 to decide if another action is needed. Thus at the function level 306, the outside party may then determine the need to communication with the patient/user 316 and access a speaker application page 318 to allow access of the outside party through the program or app to send auditory signals to the speakers of the monitoring device as well as listen in on the environment of the patient/user 320. Thus, such a line of communication is available is needed for such a purpose, whether to instruct, inquire, or notify (at least) the patient/user of anything being monitored for such a person's benefit. As before the outside party may then decide to move away from the communication portal 322, 324 and return 314, 334 to the Landing page 304 and on to the function screen 306 to possibly follow another available action. Thus, if desired, and, as should be well understood, there is no set sequence of selections of such possible actions to be undertaken by the outside party; the functions and thus actions available are simply provided in this manner as options and may be accessed in any sequence desired. Continuing, then, there is also the option for the outside party to react to a potential problem suffered by the monitored patient/user through the ability to calm such a person down from a distance through music 326 (of course, it should be understood, as well, that speaking through the system to the patient/user may also help to quell any such possible problems, and thus music playing is provided as an alternative). The outside party may thus utilize music in a therapeutic manner 328 connecting with the speaker of the monitoring device and playing any selected (and stored) music for such a purpose. The selected music thus may soothe the patient/user 330 through music, sounds, voices, and, if desired, may provide additional video presentations (not illustrated) that may act to help grab the patient/user's attention as needed. Such a system may also, if desired, include a means for the patient/user to notify the monitoring outside party if all is well and, to that end, may include a request of such a sort within the music, sounds, voice, and even possible video presentations. The patient/user may thus be instructed to select a button or icon on the monitoring device to indicate such status thereafter. As above, then, the outside party may, as desired, move away from such a music, etc., component 332 and return 334 to the Landing page 304 to further utilize the monitoring system when and for whatever needed.

Such an overall system thus allows for a patient/user the ability to remain in a self-sustaining state and location with loved ones (or other persons) allowed proper monitoring thereof with further capabilities of providing different communication and tracking operations to best ensure safety and security of such a target patient/user as needed.

Having described the disclosure in detail it is obvious that one skilled in the art will be able to make variations and modifications thereto without departing from the scope of the present invention. Accordingly, the scope of the present disclosure should be determined only by the claims appended hereto.

What I claim is:

1. A combination monitoring and communication system for utilization with a remote patient/user suffering from early onset dementia, wherein said system comprises: i) a first device residing with said remote patient that includes a base monitoring capability including a speaker function that allows an outside party to listen to the immediate environment of said remote patient/user, as well as to receive and send auditory signals thereto such an outside party, said first device further including a signal component for GPS tracking of said remote patient/user, and said first device further comprising a database of photographs of selected individuals' faces for facial recognition and identification thereof, wherein said database is associated with said speaker function to provide auditory identification of a recognized individual to said remote patient/user; and ii) at least one monitoring/communication device residing with at least one outside party, said at least one monitoring/communication device comprising a direct line auditory portal for listening to said remote patient/user environment and communicating with said remote patient/user on demand, a GPS tracking module associated with said GPS signal of said first device, and an auditory and/or video communication module for supplying music, sounds, and/or videos to said remote patient/user on demand.

2. The system of claim 1 wherein said first device database further includes auditory recordings of individual voices for identification thereof for the remote patient/user.

3. A method of monitoring a remote patient/user suffering from early onset dementia utilizing said combination monitoring and communication system of claim 1, said method comprising the steps of: i) providing said first device to said remote patient/user and initializing said device to provide monitoring thereof said remote patient/user; ii) providing at least one monitoring/communication device to said at least one outside party and initializing said monitoring/communication device to associate with said first device, thereby allowing said at least one outside party the ability to monitor, communicate, track, and transfer auditory/visual presentations to said remote patient/user, iii) activating said at least one monitoring/communication device to monitor through audio capability said remote patient/user; iv) allowing said at least one outside party to select any or all combinations of said monitor, communicate, track, and auditory/visual transfer abilities in association with said remote patient/user; and wherein said first device provides visual stimulation to said remote patient/user of auditory identifications of photographs of faces of recognized individuals from said database of photographs.

4. The method of claim 3 wherein said first device database further includes auditory recordings of individual voices for identification thereof for said remote patient/user.

* * * * *